United States Patent [19]
Dobschal et al.

[11] Patent Number: 5,999,262
[45] Date of Patent: Dec. 7, 1999

[54] PROCESS AND APPARATUS FOR DETECTING STRUCTURAL CHANGES OF SPECIMENS

[75] Inventors: Hans-Juergen Dobschal, Jena; Werner Fuchs, Cospeda; Dieter Graefe, Jena; Guenter Gauglitz, Tuebingen; Andreas Brecht, Mannweil, all of Germany

[73] Assignee: Carl Zeiss Jena GmbH, Jena, Germany

[21] Appl. No.: 08/973,653

[22] PCT Filed: Apr. 11, 1997

[86] PCT No.: PCT/EP97/01809

§ 371 Date: Dec. 18, 1997

§ 102(e) Date: Dec. 18, 1997

[87] PCT Pub. No.: WO97/40366

PCT Pub. Date: Oct. 30, 1997

[30] Foreign Application Priority Data

Apr. 19, 1996 [DE] Germany ............... 196 15 366

[51] Int. Cl.⁶ .................................................. G01B 9/02
[52] U.S. Cl. ...................... 356/357; 356/351; 356/361
[58] Field of Search .................... 356/345, 351, 356/354, 357, 361, 72, 244, 432, 445; 250/559.44; 422/82.05

[56] References Cited

U.S. PATENT DOCUMENTS

| | | |
|---|---|---|
| 4,626,684 | 12/1986 | Landa . |
| 5,234,665 | 8/1993 | Ohta et al. . |
| 5,313,264 | 5/1994 | Ivarsson et al. . |
| 5,631,171 | 5/1997 | Sandstrom et al. ............ 356/357 |
| 5,721,435 | 2/1998 | Troll ........................ 250/559.44 |

FOREIGN PATENT DOCUMENTS

| | | |
|---|---|---|
| 0 617 273 | 9/1995 | European Pat. Off. . |
| WO 95/03538 | 2/1995 | WIPO . |
| WO 95/22754 | 8/1995 | WIPO . |

*Primary Examiner*—Samuel A. Turner
*Attorney, Agent, or Firm*—McAulay Nissen Goldberg Kiel & Hand, LLP

[57] ABSTRACT

A process and a device are described for detecting physical, chemical, biological or biochemical reactions and interactions on biochemically or chemically functionalized specimen carriers in the form of layers or films from the spectral reflection after irradiation of the specimens with light of different wavelengths. In so doing, parameters for the nature of the specimens are determined in an economical and highly accurate manner and with a high degree of parallelism in the measurements. According to the process, the specimens are arranged on a substrate plate with a carrier layer of a carrier plate and are irradiated with light. The following process steps are carried out: temporally resolved illumination of an areal arrangement of specimens to be analyzed by light of different wavelengths from a tunable light source or from a scanning monochromator which is arranged subsequent to a polychromatic light source; b) the imaging of the beam component reflected on at least one boundary surface of each specimen or of the beam components or interferences reflected and interfered, respectively, at boundary surfaces of each specimen which are arranged one behind the other in the direction of light, this imaging being carried out on a spatially resolving areal detector array or a video camera by means of subsequently arranged optical elements; and c) a wavelength-selective detection of the radiation intensities reflected and influenced by the specimens or of the intensities of the imaged interferences, determination of a wavelength spectrum associated with each specimen, and derivation of parameters characterizing the interactions and reactions to be analyzed.

14 Claims, 5 Drawing Sheets

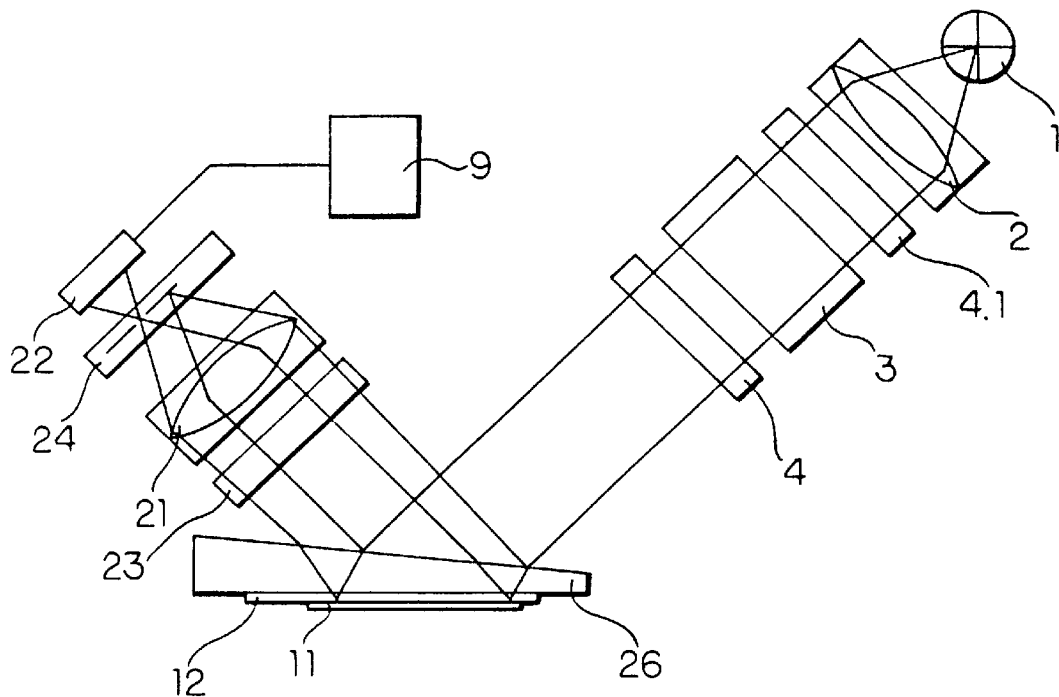
F I G. 5
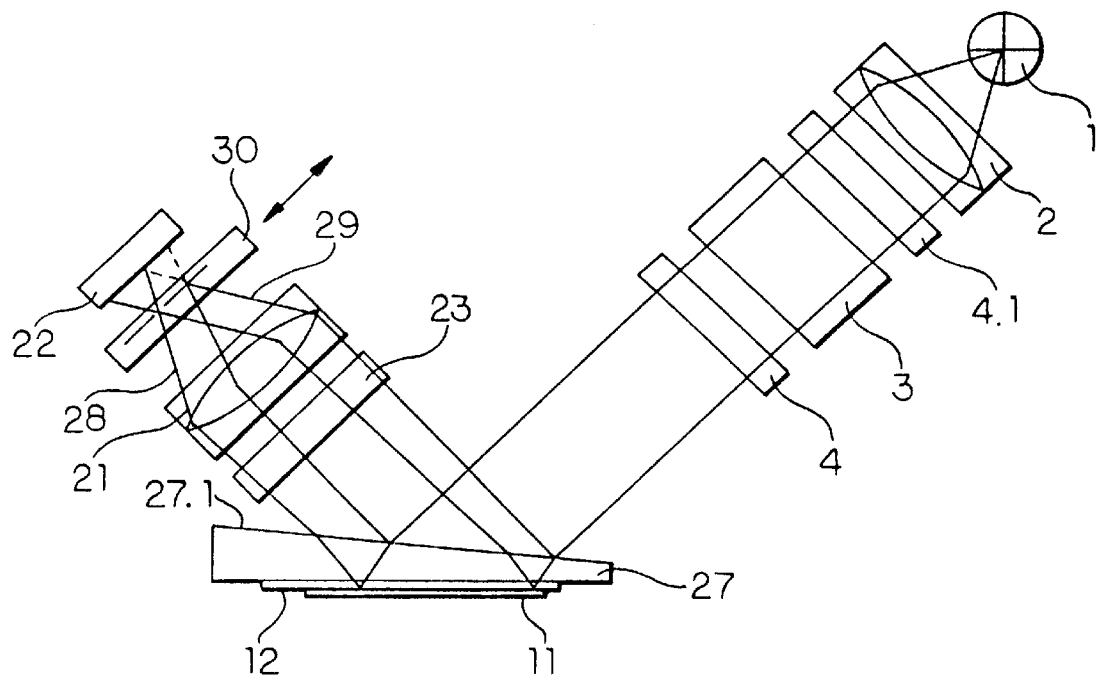
F I G. 6

PROCESS AND APPARATUS FOR DETECTING STRUCTURAL CHANGES OF SPECIMENS

BACKGROUND OF THE INVENTION a) Field of the Invention

The invention is directed to a process and a device for detecting physical, chemical, biological or biochemical reactions and interactions on biochemically or chemically functionalized specimen carriers in the form of layers or films from the spectral reflection after irradiation with light of different wavelengths. It is based on the resonance phenomenon excited by evanescent fields in planar waveguides and in thin metal films which react to changes in or attachment to the biosensitive film located thereon as well as on interference phenomena occurring as the result of reflection at the interfaces or boundary surfaces of this film.

b) Description of the Related Art

WO 93/14392 discloses a device for detecting such reactions and interactions in which collimated, polychromatic light is totally reflected at an internal prism surface. Given a suitable selection of the parameters of a spacing layer film and a cavity layer located above the latter, the occurring evanescent field is coupled into the cavity layer at resonance, wherein the resonance is effected in different wavelengths depending on the specimen interaction above the cavity layer. In a subsequent wavelength-dispersive unit, the resonance wavelength is determined as an extreme value in the spectrum.

Another arrangement for detecting biochemical interactions is known from EP 0 257 955. In this case also, polychromatic light is coupled into a transparent plate via a multiple-prism structure and is totally reflected at the transparent plate at an angle of incidence greater than the critical angle. The vertically oscillating polarization component of the evanescent field excites collective electron density oscillations (surface plasmons) in a thin metal film applied to the boundary surface. This resonance phenomenon is influenced by changes at the boundary surface due to the morphology or nature of the specimen and is detected as absorption of the respective resonance wavelength in a subsequently arranged dispersive device. The changes at the boundary surface owing to the nature of the specimen accordingly result in a shifting of the reflection minimum which is a criterion for the nature of the analyzed specimen.

WO 93/01487 describes an arrangement for the selective detection of substances in chemical, biochemical and biological measurement specimens by determining changes in the effective refractive index of a guided mode by means of a grating coupler. The grating coupler is arranged on a transparent substrate plate in the boundary surface interfacing with an applied planar waveguide and takes over the functions of input coupling and output coupling of radiation. The coupling efficiency of the entire arrangement depends upon the polarization, the angle of incidence, the waveguide characteristics, the grating characteristics, and the refractive index above the waveguide. In the input coupling optimum, a mode is excited in the waveguide and, at a determined coupling angle, the reflectivity of the grating coupler achieves a minimum which is recorded by a position-sensitive detector.

DE 42 00 088 discloses a process and a device for detecting physical, chemical, biochemical and biological processes, wherein light of a suitable wavelength or of a suitable spectral range is radiated into a specimen at which the process takes place at or in at least one thin layer of at least partially optically transparent material. In so doing, the interference phenomena which are brought about as a result of the process are detected and measured and can be interpreted and represented as a change in the optical layer thickness. For this purpose, the absolute optical layer thickness can be calculated from the spectral position of the interference extrema and their distance from one another. The optical layer thickness can also be determined from the change in intensity in one or more wavelengths. A device for carrying out the process comprises a light source emitting white light, a specimen arrangement at which the process to be studied can be carried out, a detector, for example, a photoelectric receiver array, and an evaluating device, e.g., a computer. The specimen arrangement has a base with a carrier layer comprising a thin polymer film (e.g., polysiloxane film) in which the process to be detected takes place. The base can be a glass plate, a commercially available interference filter or a suitable substrate.

All of these devices have the disadvantage that they can only be used to carry out individual measurements. The simultaneous measurement of a plurality of specimens would substantially increase technical complexity. It would only be possible to expand these measurements to a few parallel measurement objects and specimens. An example of such a device, by means of which four specimens can be measured, is described and shown in WO 93125 909.

A further disadvantage consists in that in arrangements with an angle-selective light radiation or coupling in of radiation, converting to the simultaneous measurement of a plurality of specimens requires costly duplication of the coupling structure as is illustrated in WO 92/0542.

OBJECT AND SUMMARY OF THE INVENTION

It is the primary object of the invention to provide a device for the simultaneous detection of physical, chemical, biological or biochemical reactions and interactions at or in the surface of specimens, by means of which a spectrum of the radiation intensities reflected off at least one boundary surface of the specimens can be determined in a plurality of specimens in an economical and highly accurate manner, wherein parameters for the nature of the specimens can be determined from this spectrum of radiation intensities and a high degree of parallelism can be achieved in the measurements.

According to the invention, in a process for the detection of physical, chemical and/or biochemical reactions and interactions at specimens which are arranged on a substrate plate with a carrier film of a carrier plate and which are irradiated by light via input coupling elements, the above-stated object is met by the features of the characterizing part of the first claim. A device for carrying out the process and more detailed configurations and particulars of the invention are indicated in the additional claims.

In accordance with the process, all specimens are irradiated simultaneously by light of one wavelength and the reflected light is supplied to a receiver array, e.g., a CCD array, or a video camera, and the generated electrical signals are further processed in an evaluating device which is connected with the receiver array in order to obtain measurements. After all of the specimens are evaluated with one wavelength, all of the specimens are irradiated with light of a different wavelength and measurement values of the reactions and interactions and/or of the nature of the specimens are taken again in the above-described manner. The entire spectrum of the light provided by the light source is utilized for the measurements in the described manner. In order that all of the wavelengths of a utilized wavelength range are available successively, a tunable light source or a scanning monochromator arranged subsequent to the polychromatic light source, for example, a Lyot filter, is advantageously used to illuminate the specimens.

A device, according to the invention, for carrying out the process comprises a light source which emits light of at least one wavelength which is directed onto the analyzed specimens for irradiation thereof via first optical elements and via input coupling elements arranged subsequent to the first optical elements, wherein the specimens are arranged on a substrate plate connected with a transparent carrier plate.

Second optical elements or means are provided, by which the light which is reflected by the carrier plate and influenced by the specimen is conducted to a following detector arrangement which includes photoelectric receivers, wherein the detector arrangement is connected with an evaluating device. In this device, a large number of specimens to be analyzed are arranged on a structured substrate plate of the carrier plate or are arranged directly on the carrier plate itself. In so doing, it is essential that at least the boundary surface of the specimens facing the substrate plate or carrier plate is at least partially reflecting or partly reflecting. The positions of the specimens to be analyzed on the substrate plate or carrier plate are arranged in matrix form in such a way that all of the specimens are irradiated simultaneously and in a wavelength-selective manner. The detector arrangement comprises photoelectric receivers, e.g., CCD elements, in a matrix arrangement or is a video camera. It is essential that the detector arrangement enables a spatially resolved detection of the radiation intensity which is reflected by every specimen and influenced by every specimen.

The device according to the invention makes it possible to select more than one observation wavelength and to associate the reflectivities of the individual specimens to positions of the specimens on the substrate plate. In a very advantageous manner, biochemical, physical and/or chemical processes in the specimen can be detected and quantified based on the changes in the spectral reflectivity, also by taking into account reference signals generated in a reference beam path. In particular, these processes are binding reactions which cause molecules from the specimen to attach to a sensor film arranged on the substrate plate, which leads to a localized increase in the film thickness or in the refractive index.

The boundary surfaces of the specimens located one behind the other in the direction of light are advantageously at least partially reflecting. In this way, it is possible to evaluate interferences resulting from the film thickness of the analyzed specimen. These interferences originate from the radiation components reflected at the boundary surfaces and are imaged on the detector arrangement and further processed by means of a subsequent evaluating unit to determine the specimen parameters.

In a further advantageous arrangement, the optically acting boundary surfaces of the carrier plate which are arranged successively in the direction of light extend in a parallel manner or include a small angle and are partially reflecting. In particular, in the variant with wedge-shaped carrier plate, it is possible in a simple manner to generate a reference beam path which is guided to a separate detector arrangement or, alternately with a measurement beam path, to one and the same detector arrangement. In this construction of the wedge-shaped carrier plate, a reference beam path is generated from the radiation reflected at the first (forward) boundary surface in the direction of light, and a measurement beam path is generated from the radiation that is reflected at the boundary surfaces and that is influenced by the specimens and formed by interferences and reflections, this reference beam path and measurement beam path then being guided to a shared detector arrangement or to two separate detector arrangements. A telescopic imaging system can also be arranged subsequent to the carrier plate in order to image the measurement beam path and reference beam path on a diaphragm or aperture arrangement or directly onto the detector arrangement, wherein the aperture arrangement is arranged in front of the detector arrangement. When both beam paths are imaged on one detector arrangement, the aperture arrangement can be designed so as to be switchable so that the measurement beam path and reference beam path are received alternately on the detector arrangement at different times.

The reference beam path allows the intensity distribution inside the beam bundle to be taken into account, so that an improved stability of the signal or signals can be achieved by regular measurement and by taking this distribution into account, since drift in the light source and in the following illumination system can eliminated by reference.

It is further advantageous when the specimens are irradiated vertically or obliquely through the carrier plate. With oblique radiation, in particular, disruptive reflections at the substrate plate or at the carrier plate are effectively minimized.

It is also possible to arrange the substrate plate, including the specimen located thereon, on the hypotenuse surface of a right-angle prism, wherein the illuminating light bundles can be coupled in through one short face of the prism and the measurement beam path and reference beam path can coupled out through the other short face. An isosceles prism can also be used. With this construction, evanescent fields can be generated with incident angles that are greater than the critical angles of the total internal reflection. The device can accordingly be applied to biosensors with surface plasmon resonance or with resonance reflectors.

It is further advantageous when a substance with a suitable refractive index is inserted in the space between the carrier plate and the substrate plate for adapting the refractive indices of the optically connected parts. In this way, above all, disturbing reflections can be eliminated or substantially reduced and light losses can be prevented.

The invention is explained more fully hereinafter with reference to an embodiment example.

BRIEF DESCRIPTION OF THE DRAWINGS

In the drawings

FIG. 5 a device with a wedge-shaped carrier plate without reference beam path;

FIG. 6 a device with a wedge-shaped carrier plate with reference beam path;

DESCRIPTION OF THE PREFERRED EMBODIMENTS

The process for detecting physical, chemical, biological and/or biochemical reactions and interactions at and/or in specimens that are arranged on a substrate plate with a carrier layer of a carrier plate and are irradiated, via input coupling elements, by light of a polychromatic light source comprises a temporally resolved irradiation or illumination of a surface-extensive or areal arrangement of a plurality of specimens to be analyzed by light of different wavelengths from a tunable light source or scanning monochromator which is arranged subsequent to a polychromatic light source. In a further process step, the imaging of the beam component reflected on at least one boundary surface of each specimen or the beam components or interferences reflected or interfered, respectively, at boundary surfaces of each specimen which are arranged one behind the other in the direction of light is effected on a spatially resolved areal detector array or a video camera by means of subsequently arranged optical elements. In a following step, there is carried out a wavelength-selective detection of the radiation intensities reflected and influenced by the specimens or of the intensities of the imaged interferences, the determination of a wavelength spectrum associated with each specimen, and the derivation of parameters characterizing the interactions and reactions to be analyzed.

In the following FIGS. 1 to 9, identical reference numbers are provided for identical or identically functioning elements.

Figure 1:
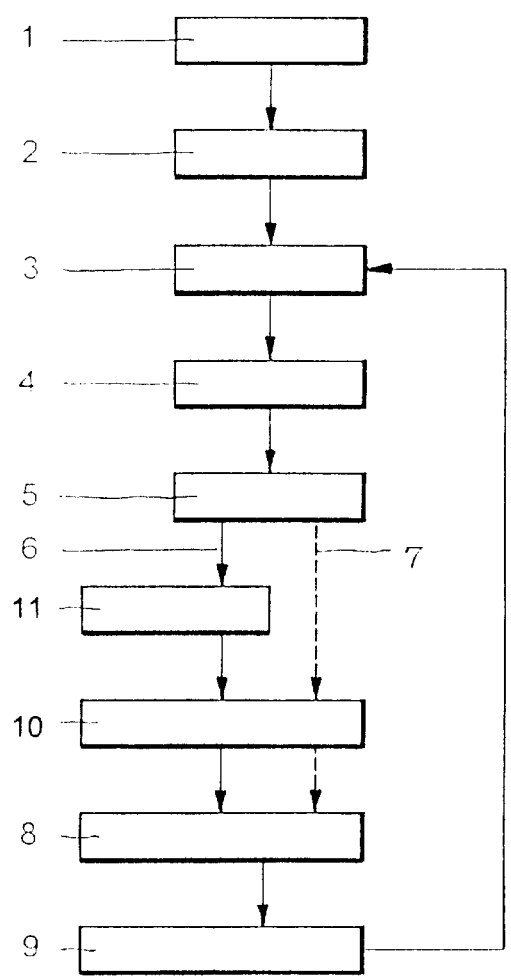
FIG. 1 a block diagram of a device according to the invention.

In accordance with the block diagram shown in FIG. 1, the device according to the invention comprises a polychromatic light source 1 which emits light of at least one wavelength. Light of a defined polarity is directed to the specimen 11 directly or via a beam splitter 5 in a measurement beam path 6 by way of a subsequently arranged collimator 2 and a monochromator 3 which generates monochromatic light of determined wavelengths, and via a polarizer 4. When a tunable light source 1 is used, e.g., a tunable laser, the monochromator can be omitted, since the wavelength to be used is adjusted at the light source in this case. Further, a reference beam path 7 is generated by the beam splitter 5. The light reflected at the surface of the specimen 11 and influenced by the specimen and the reference beam path are imaged by subsequently arranged imaging optics 10 on at least one photoelectric detector arrangement 8 which is connected with an evaluating device 9. The beam splitter 5 can also be omitted if only the light influenced by the specimen 11 is to be evaluated.

The evaluating device 9 or a computer system for control, data acquisition and evaluation makes it possible to select more than one observation wavelength and to allocate reflectivities to positions on the substrate plate carrying the specimens 11. The above-mentioned reactions and interactions at the specimens are detected and quantified based on the changes in the spectral reflectivity of the specimens, also, if required, with the inclusion of reference signals generated in the reference beam path.

Figure 2:
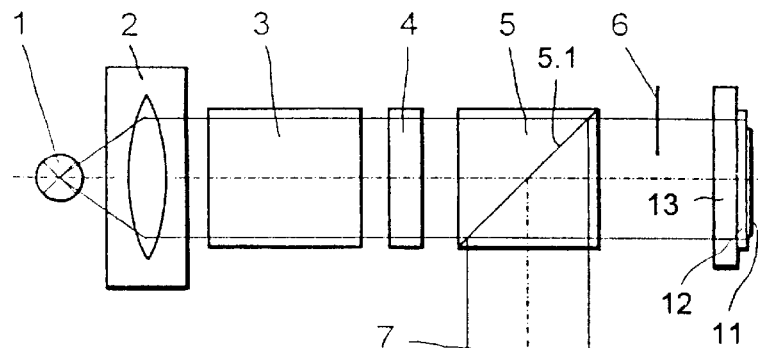
FIG. 2 a device without a reference beam path with vertical irradiation of the specimens.

The device shown in an optics diagram in FIG. 2 has the light source 1, whose radiated light is parallelized by a collimator 2. A monochromator 3 arranged after the collimator 2 generates monochromatic light which is directed vertically onto the analyzed specimen via a polarizer 4 producing a desired polarization state and via a beam splitter 5 with a beam-splitting, partially reflecting film 5.1. The specimen 11 is applied to a substrate plate 12 which is located on a transparent carrier plate 13. Thus, for example, the specimen 11 can bind to a layer system, known per se, which changes its spectral reflectivity depending on the film thickness or depending on the local refractive index. For applications in the field of biomolecular interaction, a liquid, typically aqueous, specimen is applied to a sensor film acting as a sensor. Biological components and other components from the specimen can bind at this sensor film in a selective or non-selective manner. A plurality of individual specimens 11 can be applied to the substrate plate 12 in a matrix type arrangement. Further, specificities can be generated on such a sensor film with a specimen by spatially resolved coating with various, e.g., biologically relevant, molecules. In this case, by charging the entire sensor film with a uniform specimen, information about the different binding processes can be obtained. Further, it is possible to discriminate between specific and non-specific binding effects by comparing pretreated areas and areas which have not been pretreated on the surfaces of the specimen-containing film on the substrate plate 12. Layer systems of this kind, known per se, which exhibit a change in their spectral reflectivity depending upon coverage with the specimens to be analyzed are grating couplers, thin precious-metal films, prism couplers/film waveguides or Fabry-Perot cavities. Thus, there results for the layer systems mentioned above a reflectivity extremum whose characteristic wavelength depends on the actual or current conditions at the sensor film.

The beam bundle which is reflected by the specimen-carrying surface of the substrate plate and influenced by the specimen 11 passes through the carrier plate and is deflected by the beam-splitting layer 5.1 and imaged by imaging optics 10 on a detector arrangement 8 which is connected with the evaluating device 9. The detector arrangement 8 comprises a plurality of discrete photoelectric receivers, preferably CCD elements, which are in a matrix arrangement and thus result in a spatially resolving areal detector arrangement. The imaging enables positions of specimens on the substrate plate 12 to be assigned to the individual receivers of the detector arrangement 8. If required, aperture systems (not shown) can also be provided in the beam path in order to cut out disturbing light which does not come directly from the substrate plate 12 and therefore from the specimen 11.

Figure 3:
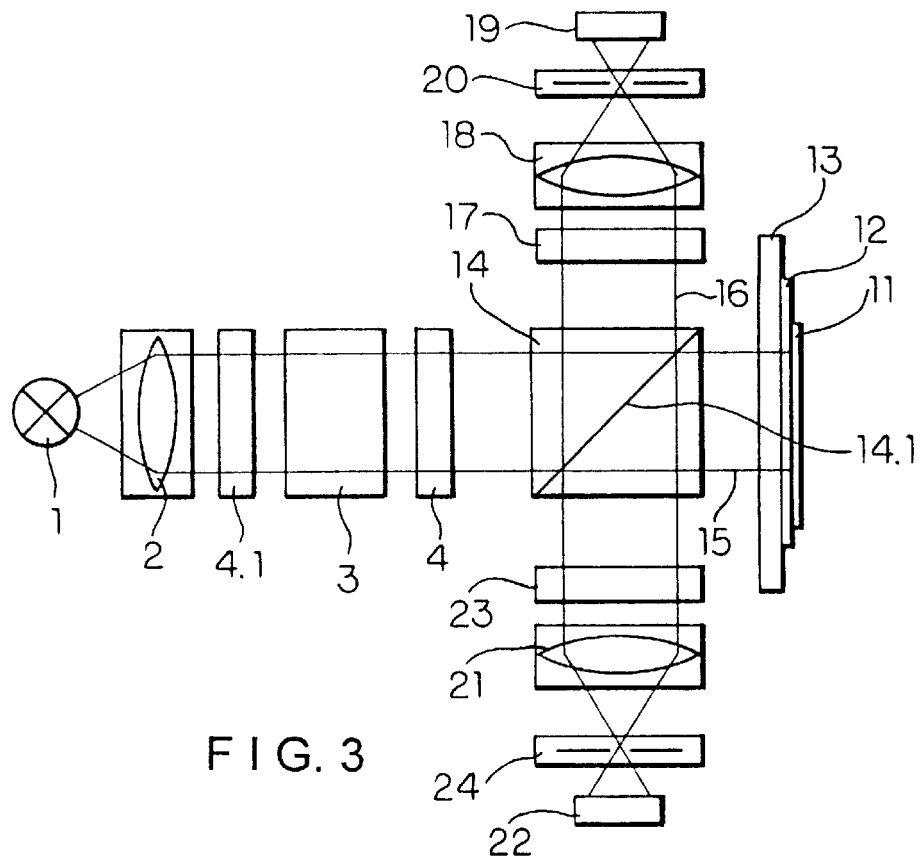
FIG. 3 a device with vertical irradiation of the specimens and with reference beam path.

In the device which is shown schematically in FIG. 3, the specimen 11 is likewise irradiated vertically. The light bundle proceeding from the light source 1 and passing through a collimator 2, a monochromator 3 and polarizers 4 and 4.1 is divided by means of a beam splitter 14 into a measurement beam path 15 and a reference beam path 16. The partial bundle forming the reference beam path 16 is imaged, without being influenced by the specimen 11, e.g., via a polarizer 17, on a detector arrangement or CCD camera 19 by an imaging system 18. Disturbing light can be excluded by an aperture 20. The partial bundle which is reflected at the specimen 11 and influenced by the specimen 11 and which forms the measurement beam path 15 is deflected at the reflecting layer 14.1 of the beam splitter 14 and is imaged on another CCD camera 22 serving as detector arrangement by an imaging system 21, wherein a polarizer 23 and an aperture 24 are likewise provided in the measurement beam path 15. The two CCD cameras 19 and 22 are likewise connected with an evaluating device (not shown).

The intensity distribution in beam bundles, for example, can be taken into account through the use of a reference beam path 16 for generating reference signals. Through regular measurement and observation of this distribution, a signal stabilization can be achieved, since drift in the light source 1 and in the further illumination beam path can be eliminated by reference. This referencing is effected, for example, by means of normalizing or standardizing the intensities found for the surface of the specimen 11 to the corresponding values for the reference beam path 16.

Figure 4:
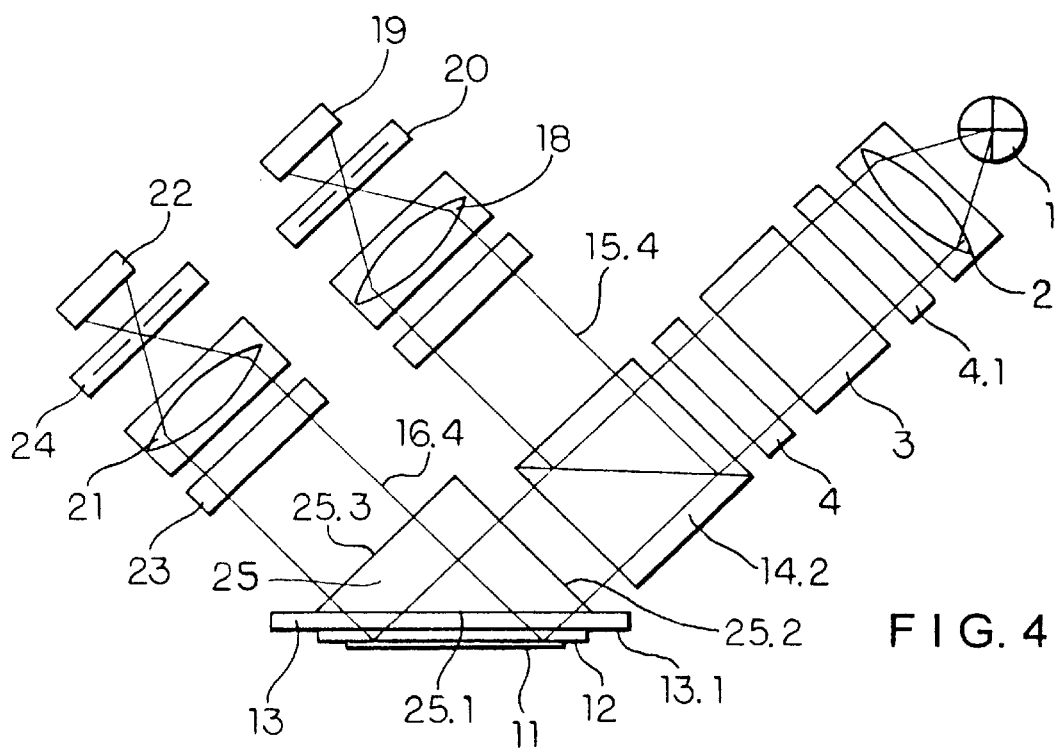
FIG. 4 a device with oblique irradiation of the specimens and with a reference beam path.

A device by means of which the specimen 11 is illuminated in an oblique beam path and which comprises a reference beam path 15 is shown in FIG. 4. The light emitted by the light source 1 is also divided in this case into a measurement beam path 16.4 and a reference beam path 15.4 by means of a beam splitter 14.2 similar to the device according to FIG. 3, wherein the beam bundle of the reference beam path 15.4 is imaged on a CCD camera 19 or detector arrangement. An input coupling prism 25 is provided in the measurement beam path 16.4, the carrier plate 13 with the substrate plate 12 and specimen 11 located thereon being arranged on the hypotenuse face 25.1 of the input coupling prism 25, wherein the illuminating light bundle enters through one short face 25.2 and the light bundle influenced by the specimen 11 exits through the other short face 25.3. Through the use of the input coupling prism 25, incident angles greater than the critical angle of total reflection can be adjusted in order to generate an evanescent field in the specimen and in the resonance structure 13.1 (e.g., waveguides, thin metal film) located below the specimen. A substance is advantageously provided for adapting the refractive index between the input coupling prism 25 and the carrier plate 13 and between the carrier plate 13 and the substrate plate 12. Alternatively, it is also possible to coat all of the surfaces so as to reduce reflection in order to prevent disturbing reflections. Instead of the right-angle prism shown in FIG. 4, a prism with an angle other than 90° or an isosceles prism can also be provided in the beam path.

FIG. 5 shows a device with wedge-shaped carrier plate 26 instead of an input coupling prism with plane-parallel carrier plate (13 in FIG. 4) arranged thereon. In this device, a reference beam path is not provided, and the illumination of the specimen 11 is effected by means of the same beam-guiding and beam-shaping optical elements as those mentioned in connection with the description of FIG. 4. Accordingly, a collimator 2 and a monochromator 3, for example, a Lyot filter, known per se, are arranged following the light source 1. The polarizers 4 and 4.1 shown in the Figure serve for the selection of the polarization directions of the illuminating beam path. The specimens 11 are again applied to a substrate plate 12, for example, wherein the substrate plate 12 is arranged on the wedge-shaped carrier plate 26, preferably with the intermediary of a substance for adapting the refractive index. This substance is not shown in FIG. 5. The specimens 11 are illuminated obliquely. The light bundle reflected by the surface of the substrate plate 12 carrying the specimens 11 and influenced by the specimens is imaged on the CCD camera 22 or on another suitable areal detector arrangement communicating with the evaluating device 9 as was already described above.

In contrast to the device according to FIG. 5, the device according to the invention shown in FIG. 6 is provided with a wedge-shaped carrier plate 27 whose surface 27.1 facing the light source 1 makes it possible to generate a measurement beam path 28 and a reference beam path 29, wherein it is reflective over the provided spectral range (for example, 400–800 $\mu$m) in such a way that the intensity of the reference beam is approximately equal to that of the measurement beam. The wedge angle of the carrier plate 27 is in the order of magnitude of less than 2°. The light emitted by the light source 1 is radiated obliquely onto the carrier plate 27 by means of optical elements arranged between the light source 1 and carrier plate 27. The light bundle reflected at the surface 27.1 forms the reference beam path 29 and is imaged on the CCD camera 22 via the polarizer 23 by means of the imaging system 21. The light bundle which passes through the wedge-shaped carrier plate 27 and substrate plate 12 located thereon and which forms the measurement beam path 28 is reflected at the surface of the substrate plate 12 carrying the specimens 11 so as to be influenced by the specimens and is imaged on the CCD camera 22 by the same elements as the reference beam path 29. Through the use of the wedge-shaped carrier plate 27 and by means of the reflection of the light at surfaces lying in different planes in the direction of light, an angle is generated between the measurement beam path and the reference beam path with the result that these beam paths are divided or separated and, accordingly, the beam components impinging on different positions on the CCD camera 22 or detector arrangement are alternately separated by means of an aperture system 3 arranged upstream. For example, the measurement beam path and reference beam path can be evaluated alternately by a displacement of the aperture system 30.

The device shown in FIG. 6 also makes it possible to receive and correspondingly evaluate interferences depending on the film thickness of the specimens 11. These interferences originate through reflection of the light at the surface of the substrate plate 12 carrying the specimens 11 and at the free surface of the specimens 11. The film thickness which constitutes a measurement for the reactions and interactions to be analyzed can be determined from the interferences generated at different wavelengths.

Figure 7:
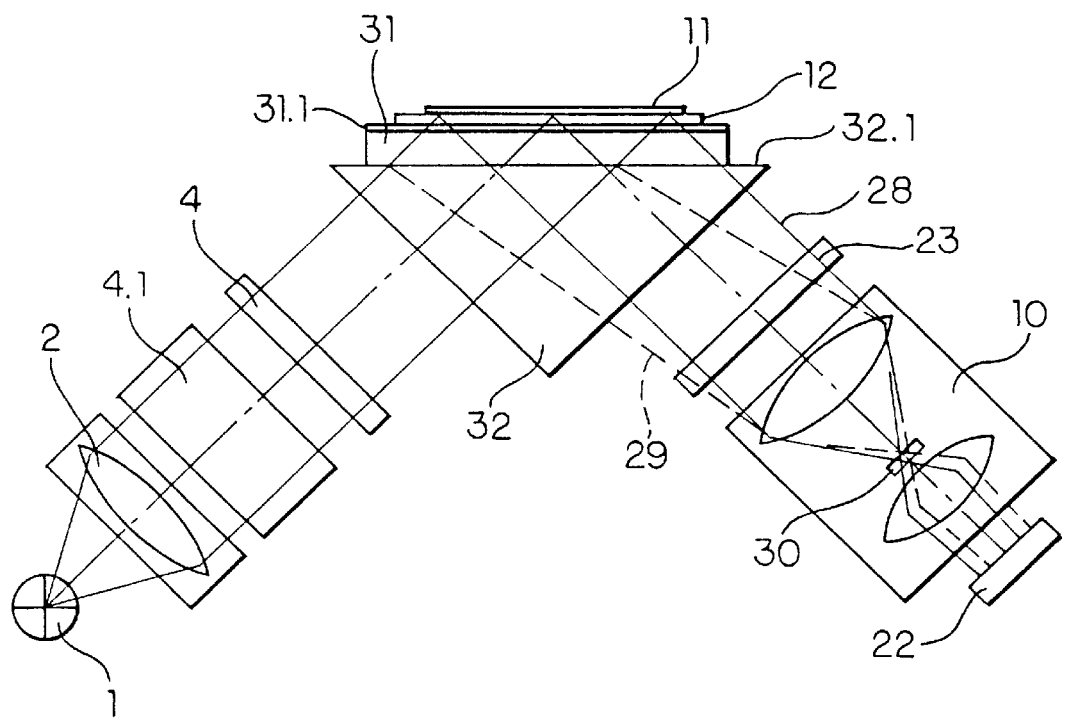
FIG. 7 a device with prism coupler and wedge plate.

FIG. 7 shows a device with a wedge-shaped carrier plate 31 with a resonance structure 31.1, wherein this carrier plate 31 is arranged on the hypotenuse face 32.1 of a coupling prism 32, advantageously with the intermediary of a substance adapting the refractive indices of the connected parts. In this case also, an angle is generated between the measurement beam path 28 and the reference beam path 29 by the action of the wedge-shaped carrier plate 31, so that a separation of these beam paths is enabled at different positions on the detector arrangement or CCD camera 24. The two beam paths can be imaged alternately by means of an intermediately arranged and advantageously displaceable aperture 30. This arrangement is especially suitable for carrying out a large number of measurements for detecting reactions and interactions of the type mentioned above by making use of surface plasmon resonance, wherein the coupling prism 32 serves for coupling in and coupling out the beam paths with low losses. The polarizers 4 and 4.1 shown in the drawing are provided for selecting the polarization directions of the illuminating beam paths. Normally, the polarization plane located vertical to the incident plane of the beams is used. In other possible arrangements, a polarization plane extending at a 45-degree angle is selected in the input coupling beam path. In the output coupling beam path, the polarizer 23 is rotated by 90 degrees with reference to polarizer 4.

Figure 8:
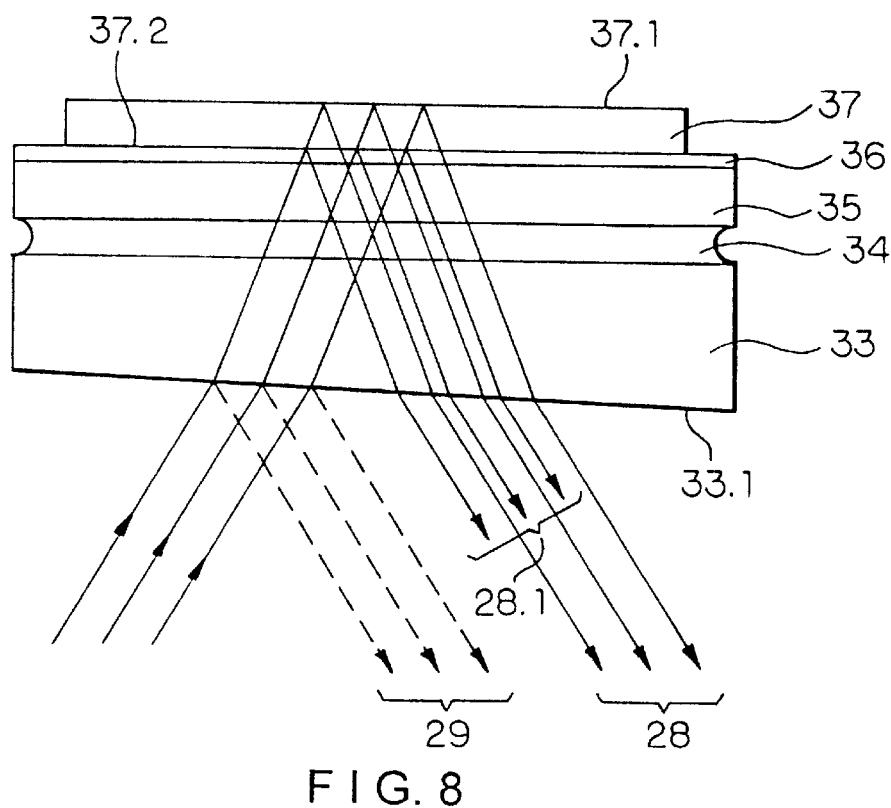
FIG. 8 an exemplary construction of a carrier plate and the arrangement of the substrate plate.

FIG. 8 shows a wedge-shaped carrier plate 33 on which the substrate plate 35 is arranged with the intermediary of a substance 34 serving to adapt the refractive index. The substrate plate 35 advantageously carries a film 37 which is, for example, biospecific or chemospecific, likewise with the intermediary of another substance 36, the specimen to be analyzed being located on or in this film 37. The surface 33.1 facing the light source is partially reflecting. The light which is reflected at it and which is not affected by the specimen forms the reference beam path 29, and the light which is reflected at surface 37.1 and influenced by the specimen forms the measurement beam path 28. The specimen can influence the film or the characteristics of the film in such a way, among others, that the reflectivity of the surface 37.1 or the film thickness is changed and is a measurement for the reaction or interaction to be analyzed.

The arrangement according to FIG. 8 shows the beam configuration such as it is realized in determining the reflectivity of the film 37. For example, if the specimen causes a change in the thickness of the film 37, the beam bundles 28 and 28.1 reflected at the two surfaces 37.1 and 37.2 are caused to interfere, these interferences are imaged on the receiver arrangement and the generated signals are further processed.

Figure 9:
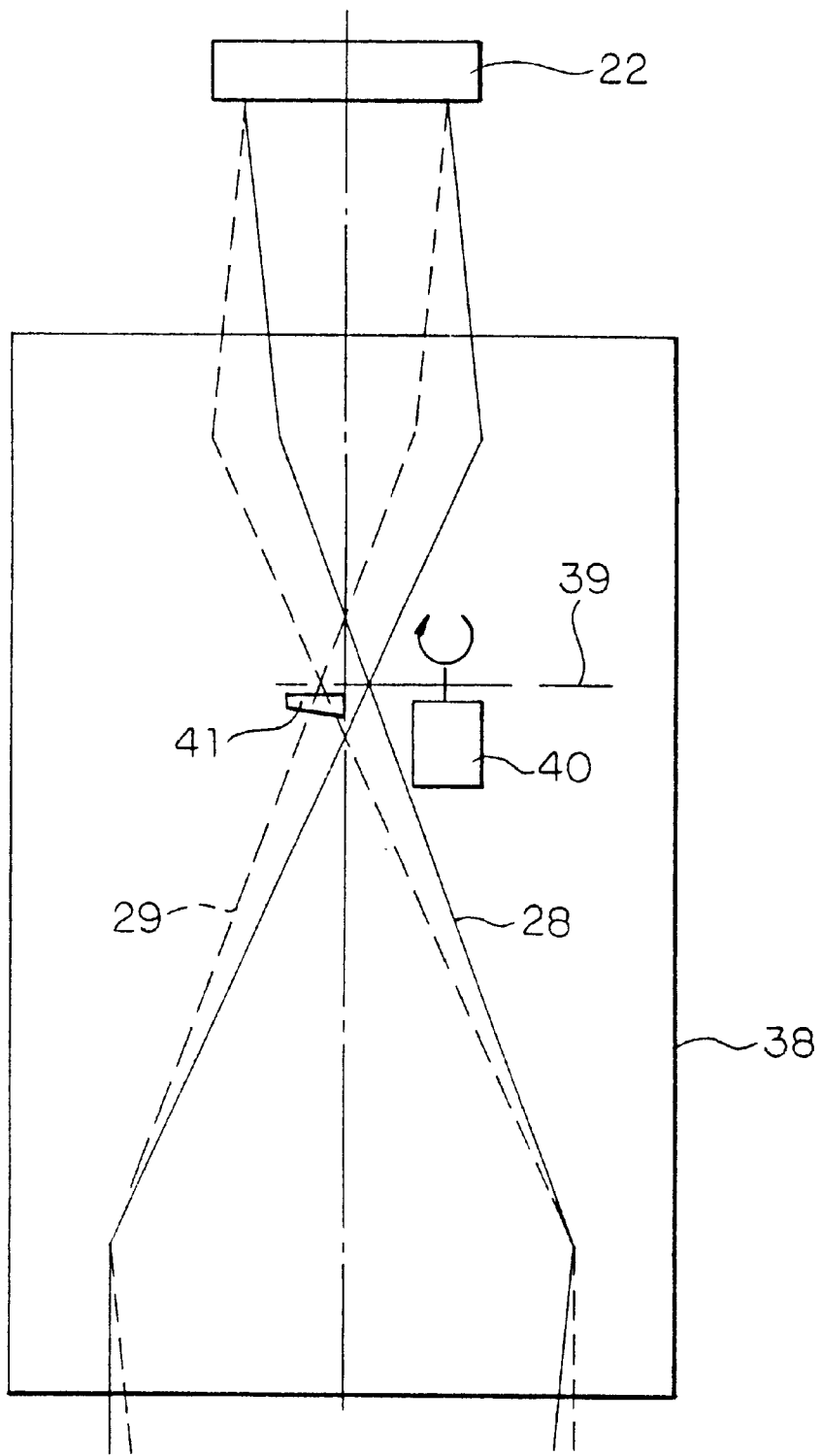
FIG. 9 telescopic imaging optics of the device with aperture switching.

FIG. 9 shows the beam path of a telescopic imaging optical system 38 with the possibility of aperture switching. For this purpose, an adjustable aperture 39 is provided in the focussing plane in which the measurement beam path and reference beam path are imaged. This aperture 39 is preferably switchable by driving means 40 in such a way that the measurement beam path and reference beam path can be imaged alternately on the detector arrangement 8. By means of a deflecting prism 41 in the reference beam path 29, the measurement beam path 28 and the reference beam path 29 are imaged at the same location on the detector arrangement 8. This deflecting prism 41 compensates for the deflection (divergence) of the two beam paths 28 and 29 on the detector plane which is produced by the wedge-shaped carrier plate, not shown in FIG. 9, so that different sensitivities of the pixel type receivers can also be eliminated by reference.

While the foregoing description and drawings represent the present invention, it will be obvious to those skilled in the art that various changes may be made therein without departing from the true spirit and scope of the present invention.

What is claimed is:

1. A process of detecting structural changes of specimens of substances arranged on a substrate plate with a carrier film of a carrier plate and which are irradiated by light via optical input elements, the process comprising the steps of:
   a) irradiating all of said specimens simultaneously;
   b) illuminating an areal arrangement of said specimens to be analyzed by monochromatic light of one wavelength;
   c) imaging light reflected from each of said specimens onto an areal detector array;
   d) processing electrical signals generated by said detector array in an evaluating device connected to said detector array;
   e) after all of said specimens have been evaluated by said evaluating device with said one wavelength, repeating steps b) to d) with monochromatic light of a second wavelength;
   f) making a wavelength-selective detection of radiation intensities reflected by said specimens;
   g) determining a wavelength spectrum associated with each of said specimens; and
   h) deriving from said determined wavelength spectrum a plurality of parameters characterizing structural changes in the specimens.

2. Apparatus for detecting structural changes of specimens, comprising:
   a light source adapted to emit monochromatic light of one wavelength;
   optical elements adapted to collimate the emitted light to produce collimated light;
   a transparent carrier plate adapted to receive a substrate plate having an areal arrangement of specimens to be analyzed thereon;
   optical means for deflecting the collimated light onto the carrier plate, said deflected collimated light being influenced by all of said specimens simultaneously;
   a detector arrangement including photoelectric receivers;
   second optical means for directing light influenced by said specimens to said photoelectric receivers of said detector arrangement;
   an evaluating device coupled to receive outputs of said photoelectric receivers for evaluating the influences of each to said specimens; said evaluating device controlling said light source to emit monochromatic light of a second wavelength after all of said specimens have been evaluated with said first wavelength;
   means for making a wavelength-selective detection of radiation intensities reflected by said specimens from the evaluations determined by said evaluating device;
   means for determining a wavelength spectrum associated with each of said specimens; and
   means for deriving from said determined wavelength spectrum a plurality of parameters characterizing structural changes in the specimens.

3. The apparatus of claim 2, wherein boundary surfaces of specimens located one behind the other in the direction of light are at least partially reflecting, and interferences generated from the radiation reflected at boundary surfaces are imaged on the detector arrangement.

4. The apparatus of claim 2, wherein optically acting surfaces of the carrier plate arranged successively in the direction of light extend in a parallel manner or include a small angle and are partially reflecting.

5. The apparatus of claim 2, wherein the specimens are irradiated through the carrier plate.

6. The apparatus of claim 2, wherein a vertical or an oblique irradiation of the specimens is provided.

7. The apparatus of claim 2, wherein partially reflecting surfaces of a specimen receptacle include a small angle so that radiation which is reflected at the carrier plate and caused to interfere is split into a measurement beam path and a reference beam path, wherein at least one areal detector arrangement is associated with the measurement beam path and with the reference beam path.

8. The apparatus of claim 2, wherein a detector arrangement each is associated with a measurement beam path and a reference beam path.

9. The apparatus of claim 2, wherein a reference beam path is provided which is generated by reflection of radiated light at surfaces of the carrier plate and a measurement beam path is provided which is generated by reflection and interference of the radiated light at a surface of an arrangement of the specimens and at the specimen surface and which is influenced by the film thickness of the specimens, and wherein a telescopic imaging system for imaging the measurement beam path and reference beam path on an aperture arrangement or on the detector arrangement is provided, and wherein the aperture arrangement is arranged in front of the detector arrangement.

10. The apparatus of claim 9, wherein the aperture arrangement is switchable such that the measurement beam path or the reference beam path can be imaged on the detector arrangement.

11. The apparatus of claim 2, wherein the substrate plate with the specimens located thereon is arranged above a surface plasmon resonator on the hypotenuse face of a right-angle prism or isosceles prism, wherein an illuminating light bundle can be coupled in through a short face of the prism and a measurement beam path or a reference beam path can be coupled out through the other short face of the prism.

12. The apparatus of claim 2, wherein a substance with a suitable refractive index is inserted in the space between the carrier plate and the substrate plate to prevent disruptive reflections and for adapting the refractive index.

13. The apparatus of claim 2, further comprising layer systems in the form of grating couplers, thin precious-metal films, prism couplers with film waveguides or Fabry-Perot cavities for receiving the analyzed specimens and interactions.

14. The process of claim 1, wherein after all of said specimens have been evaluated by said evaluating device with said second wavelength, steps b) to d) are repeated with monochromatic light of a third wavelength.

* * * * *